United States Patent
Predick (10) Patent No.: US 9,456,846 B2
(45) Date of Patent: Oct. 4, 2016

(54) DIRECTIONAL SEQUENTIAL DILATION SYSTEM WITH NEURO MONITORING

(71) Applicant: Life Spine, Inc., Huntley, IL (US)

(72) Inventor: Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 38 days.

(21) Appl. No.: 14/135,238

(22) Filed: Dec. 19, 2013

(65) Prior Publication Data

US 2014/0172002 A1 Jun. 19, 2014

Related U.S. Application Data

(60) Provisional application No. 61/739,137, filed on Dec. 19, 2012.

(51) Int. Cl.
| | |
|---|---|
| *A61M 29/00* | (2006.01) |
| *A61B 17/34* | (2006.01) |
| *A61B 17/02* | (2006.01) |
| *A61B 17/00* | (2006.01) |

(52) U.S. Cl.
CPC ......... *A61B 17/3417* (2013.01); *A61B 17/025* (2013.01); *A61B 17/3421* (2013.01); *A61B 2017/00261* (2013.01); *A61B 2017/0262* (2013.01)

(58) Field of Classification Search
CPC .......... A61B 17/3417; A61B 17/3421; A61B 17/024; A61B 17/1757; A61B 2017/3433; A61B 2017/00261; A61B 2017/02625; A61B 17/025; A61B 17/3439; A61B 17/0218; A61F 2/4611
See application file for complete search history.

(56) References Cited

U.S. PATENT DOCUMENTS

2011/0208226 A1* 8/2011 Fatone et al. .................. 606/191
2014/0303666 A1* 10/2014 Heiman et al. ................ 606/198

* cited by examiner

*Primary Examiner* — Diane Yabut
(74) *Attorney, Agent, or Firm* — Foley & Lardner LLP (57) ABSTRACT

A directional sequential dilation system includes a dilation tube assembly having a plurality of cylindrical, nesting directional dilation tubes including an initial cylindrical dilation tube that provides a passage for neuro-monitoring. Subsequent cylindrical directional dilation tubes sequentially increase in size including the increase in diameter. Each tube is configured to nest onto a previous cylindrical directional dilation tube via an off-centered structure formed in each of the subsequent cylindrical directional dilation tubes. The off-centered cutouts allow the subsequent cylindrical dilation tubes to dilate the soft tissue while at the same time sequentially migrate the incision dilation in a particular direction and distance from the initial cylindrical dilation tube insertion point (i.e. the initial neuro-monitoring insertion point). The directional sequential dilation system is particularly useful in spinal surgery.

11 Claims, 9 Drawing Sheets

DIRECTIONAL SEQUENTIAL DILATION SYSTEM WITH NEURO MONITORING

CROSS-REFERENCE TO RELATED APPLICATIONS

This patent application claims the benefit of and/or priority under 35 U.S.C. §119(e) to U.S. Provisional Patent Application Ser. No. 61/739,137 filed Dec. 19, 2012, entitled "Dilation Tube System For Neuro Monitoring And Incision Dilation In Spinal Surgery" the entire contents of which is specifically incorporated herein by this reference.

BACKGROUND OF THE INVENTION

1. Field of the Invention

The present invention relates to devices used in spinal surgery and, more particularly, to devices for neuro monitoring and incision dilation in spinal surgery.

2. Background Information

When performing typical spinal surgery it is necessary for the surgeon to contend with and manage various aspects of the procedure. A major aspect of spinal surgery is being able to determine position of a nerve or nerves that are proximate the surgical site. This is necessary to avoid cutting or damaging the nerve or nerves during the surgical procedure.

After an incision is made the surgeon locates any spinal nerve or nerves at or proximate the surgical site (i.e. neuro monitoring) before the soft tissue is dilated in order to gain access to the specific surgical area. Currently, the process of neuro monitoring and then dilating the soft tissue to gain access to the specific surgical site involves using a sequence of right-cylinder dilation tubes of increasing diameters. After an initial or first right-cylinder dilation tube is inserted into the incision for neuro monitoring, additional right-cylinder dilation tubes of increasing diameter are positioned over each other until the specific surgical area is reached.

The problem with the prior art approach is that current sequence of right-cylinder dilation tubes dilate the incision circumferentially which keeps the center point of the initial right-cylinder dilation tube and the main working channel the same. With the prior art method, the surgeon must continually neuro monitor and potentially adjust the position of the working channel since the prior art right-cylinder dilation tubes grow circumferentially in diameter in all directions—which is both towards and away from the nerve position.

It is therefore an object of the present invention to overcome the prior art deficiencies of neuro monitoring and incision dilation for spinal surgery.

SUMMARY OF THE INVENTION

A system and method for directional and sequential incision dilation with neuro monitoring uses an assembly of separate nesting tubes. Each dilation tube of the dilation tube assembly is configured to provide incision dilation migration in a given direction, distance and angle from an initial dilation tube of the dilation tube assembly that has been inserted in an initial neuro-monitoring area.

The dilation tube assembly comprises a plurality of cylindrical, nesting dilation tubes including an initial cylindrical dilation tube that provides a passage for a neuro-monitor. Subsequent cylindrical dilation tubes sequentially increase in size along of increasing diameter each one configured to nest onto a previous cylindrical dilation tube via an off-centered channel, notch or cutout formed in each of the subsequent cylindrical dilation tube. The off-centered cutouts allow the subsequent cylindrical dilation tubes to dilate the soft tissue while at the same time migrate the incision dilation in a particular direction at some angle and/or distance from the initial cylindrical dilation tube insertion point (i.e. the initial neuro-monitoring insertion point). Nesting provides a stable construct.

In one form, the initial cylindrical dilation tube is a right-cylinder tube while each subsequent cylindrical dilation tube is an elliptic cylinder tube with a notch or cutout in one wall. The initial dilation tube has a closed passage for a neuro monitoring device. The elliptical configuration provides the directional incision migration. Each notch or cutout is has ends configured and sized to nest onto or fit around a nesting portion of the previous cylindrical dilation tube. Other manners of nesting subsequent cylindrical dilation tubes to provide directional (non-equidistant) incision migration relative to an initial neuro-monitoring insertion point may be used.

The present dilation tube assembly is preferably, but not necessarily, used in conjunction with a spinal retractor during the spinal surgery. The spinal retractor includes a posterior blade that is shaped to receive the dilation tube assembly. The posterior blade may or may not be offered without any angulation capabilities for additional rigidity of the construct. The dilation tube assembly permits determination of nerve position then dilating anteriorly (or away from retractor blades) for a known safe placement of the retractor blades. An arm of the retractor that carries the static blade (and which cradles the dilation tube assembly) includes a threaded table attachment bore along with guide holes posterior of the static blade wall for insertion of a neuro-monitoring sounding probe following insertion of retractor/blades if double checking of nerve is desired.

The present invention will be more apparent upon reading the following detailed description in conjunction with the accompanying drawings.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Like reference numerals indicate the same or similar parts throughout the several figures.

A detailed description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF THE PREFERRED EMBODIMENT

Figure 1:
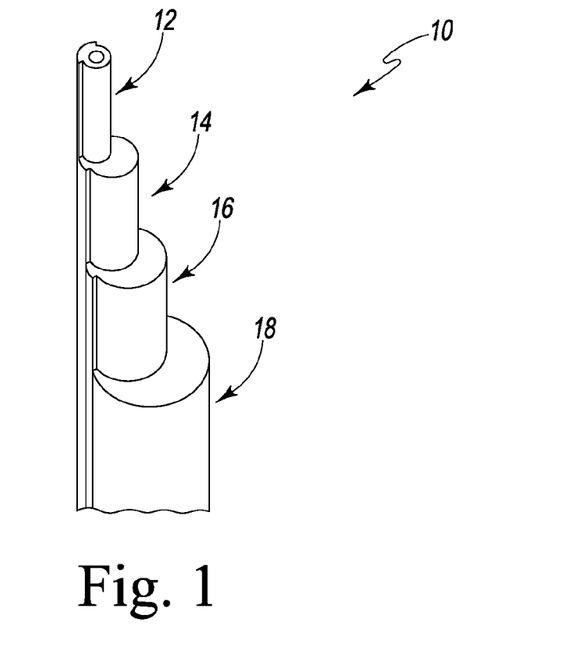
FIG. 1 depicts an exemplary embodiment of an assembled dilation tube system fashioned in accordance with the present principles.

Referring to FIG. 1 there is depicted a view of an upper portion of an exemplary embodiment of a directional sequential dilation tube assembly ("dilation tube assembly"), generally designated 10, fashioned in accordance with the present principles, the dilation tube assembly providing directional and sequential incision dilation migration of a given direction, distance and angle from an initial neuro-monitoring insertion point versus prior art equidistant incision dilation migration from an initial neuro-monitoring insertion point—particularly when used in conjunction with a spinal retractor.

The exemplary embodiment of a dilation tube assembly 10 shown in FIG. 1 and throughout the various figures has four (4) dilation tubes 12, 14, 16 and 18. It should be appreciated that the number of dilation tubes may be more or less than four (4) but can be no less than two (2). The dilation tubes are made from a suitable surgical grade material such as stainless steel, titanium, Aluminum or the like and are preferably, but not necessarily, cylindrical tubes. The cylindrical dilation tube 12 is an initial dilation tube while the cylindrical dilation tubes 14, 16 and 18 are subsequent sequential dilation tubes. Further dilation tubes (not shown) of the dilation tube assembly would be further subsequent sequential dilation tubes. As seen in FIG. 1, the dilation tubes stack upon one another in a nesting fashion such that they are together when assembled. As explained further below, because of their shape the dilation tubes dilate soft tissue of an incision (not shown) while at the same time migrate the incision dilation in a particular direction, distance and angle direction from the initial cylindrical dilation tube insertion point (i.e. the initial neuro-monitoring insertion point as provided by the initial dilation tube) while allowing continuous neuro monitoring via the initial dilation tube from the same location.

Figure 2:
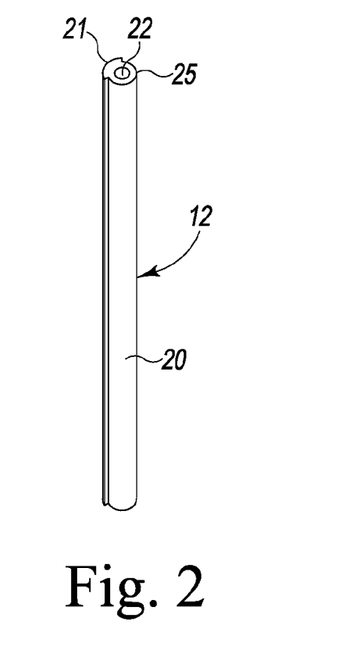
FIG. 2 is an isometric view of an initial dilation tube of the present dilation tube system.
Figure 3:
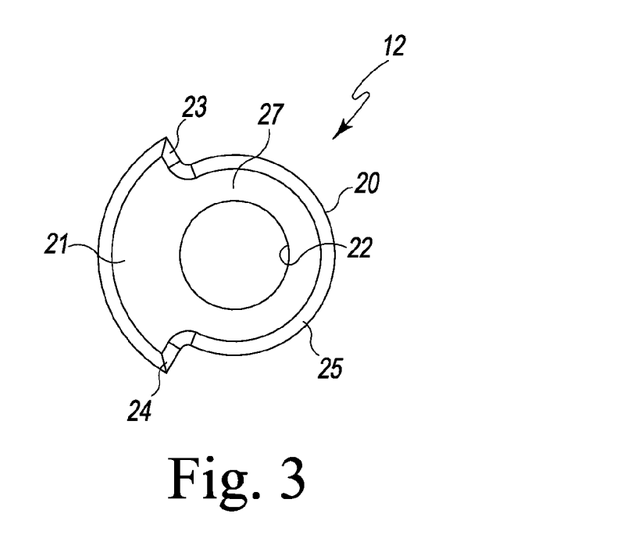
FIG. 3 is an enlarged top view of the initial dilation tube of FIG. 1.

The initial dilation tube 12 is particularly shown in FIGS. 2 and 3. The initial dilation tube 12 is defined by a generally right cylinder body 20 having a rounded longitudinal flange, rib, projection or the like 21 and a longitudinal bore 22. An upper end 27 of the body 20 is generally planar. The longitudinal bore 22 extends the length of the right cylinder body 20 and provides a passage or channel for a neuro probe, device or the like. The initial dilation tube 12 is inserted into the incision such that a neuro monitoring probe, device or the like (or other type of device) 5 extends through the bore 22 (see, e.g., FIG. 16). The outer surface of the body 20 is preferably smooth, including that of the longitudinal rib 21. The outside surface of the body 20, as well as the bodies of the other dilation tubes, may be coated or otherwise made to provide a smooth surface.

Figure 11:
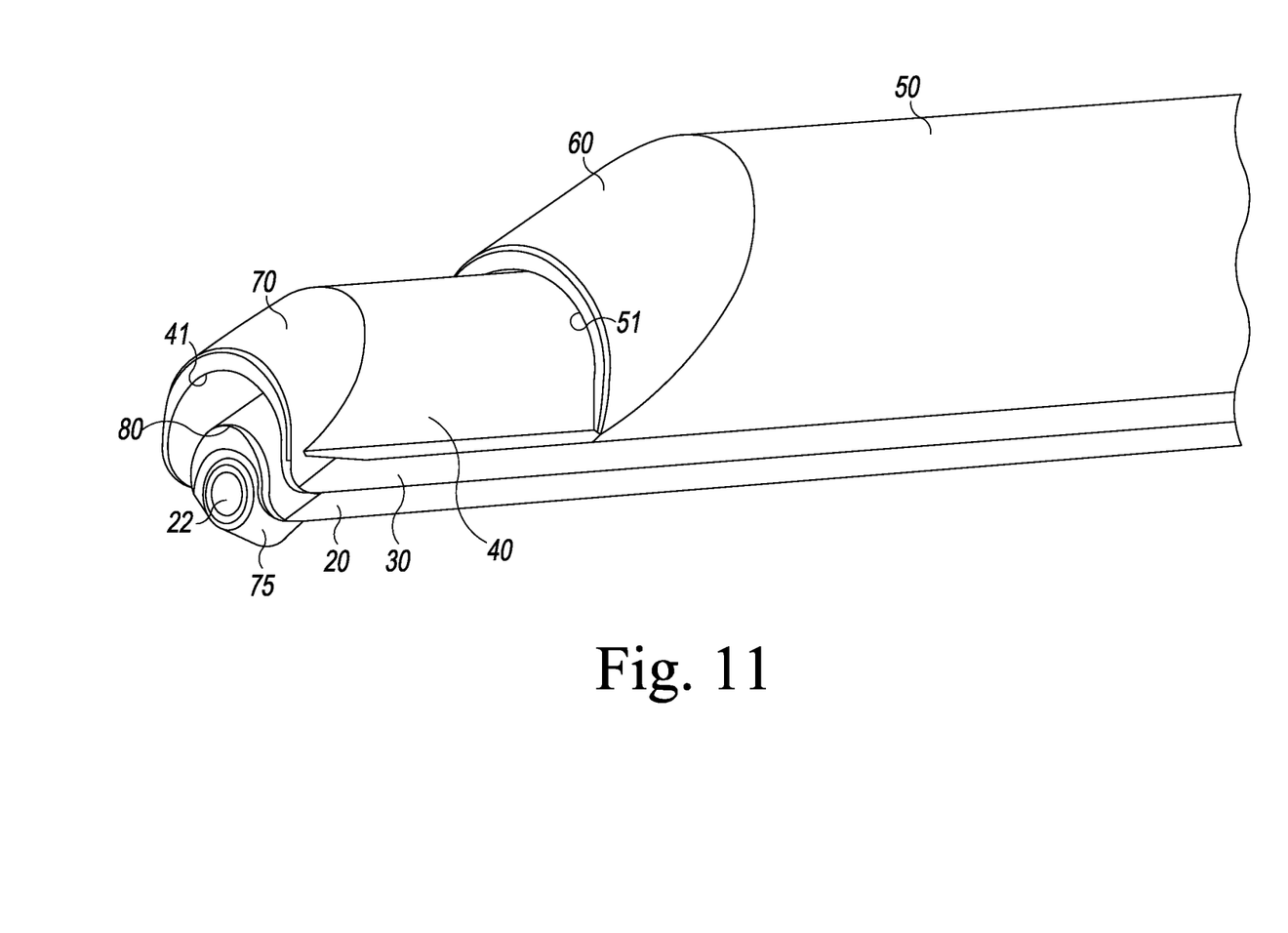
FIG. 11 is an enlarged partial view of the assembled initial, secondary and tertiary dilation tubes with the quaternary dilation tube having a beveled tip shown being slid over the tertiary dilation tube.

In FIG. 3, an enlarged view of a top of the initial dilation tube 12 is shown to particularly envision its longitudinal and cross-sectional shape and/or configuration. As discerned, the longitudinal flange 21 has a rounded outer surface in like manner and preferably, but not necessarily, concentric with the outer surface of the body 20. A beveled or angled edge 25 provides a transition between the upper ends of the body 20 and the longitudinal rib 21. The longitudinal rib 21 extends from the body 20 at a first longitudinal transition 23 on one side of the rib 21 and at a second longitudinal transition 24 on another side of the rib 21. The first longitudinal transition 23 creates or defines a first shelf or ledge providing a first seat for a first subsequent dilation tube 14. The second longitudinal transition 24 creates or defines a second shelf or ledge providing a second seat for the first subsequent dilation tube 14. As seen in FIG. 11, the initial dilation tube 12 has a rounded lower end 75.

The dilation tube 12 is the first or initial tube of the dilation tube assembly to be inserted into the incision. The bore 22 of the initial dilation tube 12 permits a monitoring probe 5 or the like to be positioned adjacent a nerve or nerves (neuro-monitoring) once an incision has been made and/or positional stability through which a guide wire, probe, device or the like can be inserted. In this first stage of incision dilation, the initial dilation tube 12 inserted into the incision is preferably, but not necessarily, generally a right-cylinder so as to initially provide a generally equidistant incision dilation area.

Figure 4:
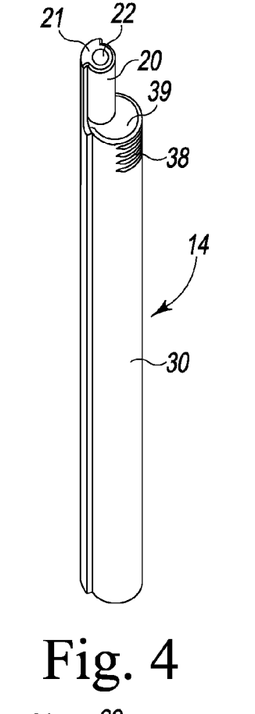
FIG. 4 is an isometric view of the initial dilation tube and a secondary dilation tube assembled thereon of the exemplary dilation tube system of FIG. 1.
Figure 5:
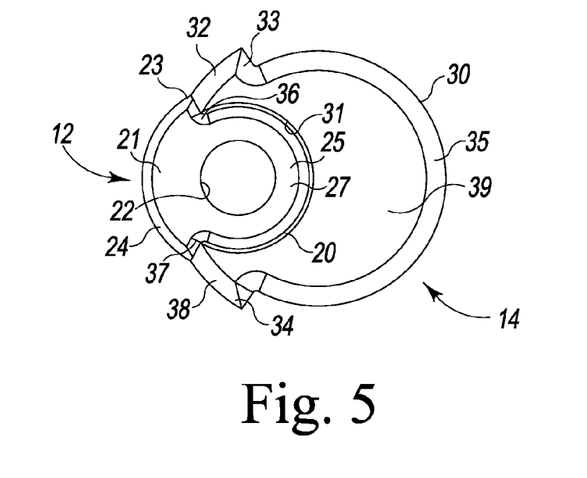
FIG. 5 is an enlarged top view of the assembled initial and secondary dilations tubes of FIG. 4.

Referring to FIGS. 4 and 5 there is depicted a second stage in assembly of the dilation tube structure 10 wherein the first subsequent directional dilation tube 14 is sequentially situated onto the initial dilation tube 12. The outer shape and configuration of the initial dilation tube 12 allows the nested reception of the first subsequent directional dilation tube 14 via its nesting structures. The first subsequent directional dilation tube 14 is defined by a generally elliptic cylinder body 30 having a generally elliptical outer surface and a rounded longitudinal notch, cutout, channel or the like 31. An upper end 39 of the body 30 is generally planar. The longitudinal channel 31 extends the length of the elliptic cylinder body 30 and provides a reception site for the initial dilation tube 12 as the first subsequent directional dilation tube 14 is received onto the initial dilation tube 12 during the second stage of incision dilation per the present method. The outer surface of the body 30 is preferably smooth, including the inner surface of the longitudinal channel 31. An upper portion of the outer surface of the body 30 may include arced notches 38.

Referring to FIG. 5, an enlarged view of a top of the first subsequent directional dilation tube 14 is shown to particularly envision its longitudinal and cross-sectional shape and/or configuration. As discerned, the longitudinal channel 31 has a rounded inner surface, shape and size complementary to the outer surface of the body 20 of the initial dilation tube 12 in order to be received on or nest upon the initial dilation tube 12. The nesting structures include a first longitudinal flange 32 provided at a first edge or end 36 of the channel 31 and a second longitudinal flange 38 provided at a second edge or end 37 of the channel 31. The shape of the first end 36 is complementary to the shape of the first transition 23 such that the first end 36 of the first subsequent dilation tube 14 seats or nests against the first transition 23 of the initial dilation tube 12. The shape of the second end 37 is complementary to the shape of the second transition 24 such that the second end 37 of the first subsequent directional dilation tube 14 seats or nests against the second transition 24 of the initial dilation tube 12. A beveled or angled edge 35 provides a transition between the upper ends of the body 30 and first and second flanges 32, 38.

The first flange 32 extends from the body 30 at a first longitudinal transition 33 and is generally arc-shaped and preferably, but not necessarily, concentric with the outer surface of the body 30. The second flange 38 extends from the body 30 at a second longitudinal transition 34 and is generally arc-shaped and preferably, but not necessarily, concentric with the outer surface of the body 30. The first longitudinal transition 33 creates or defines a first shelf or ledge providing a first seat for a second subsequent directional dilation tube 16. The second longitudinal transition 34 creates or defines a second shelf or ledge providing a second seat for the second subsequent dilation tube 16. As seen in FIG. 11, the first subsequent directional dilation tube 14 has a rounded lower end 80.

The first subsequent directional dilation tube 14 is configured as an elliptical cylinder with the channel 31 disposed in a side thereof. As such the tube 14 has an elliptic portion 39 that projects outwardly from the channel 31. Direction of the elliptic portion 39 provides the direction of incision dilation. Rotational orientation of the initial dilation tube 12 determines the angle and direction of incision dilation by the orientation of the first and second transitions 23, 24 since the first subsequent directional dilation tube nests onto the initial dilation tube 12.

The first subsequent directional dilation tube 14 is the second dilation tube to be inserted into the incision. The bore 22 of the initial dilation tube 12 still permits monitoring position of the nerve or nerves (neuro-monitoring) while the incision is dilated away from the nerve (e.g. anteriorly) in the desired angle as determined by the rotational orientation of the initial dilation tube 12. In this second stage of incision dilation, the first subsequent directional dilation tube 14 inserted over the initial dilation tube 12 and into the incision. The elliptical configuration of the body 30 migrates the incision dilation towards the direction of the ellipse.

Figure 6:
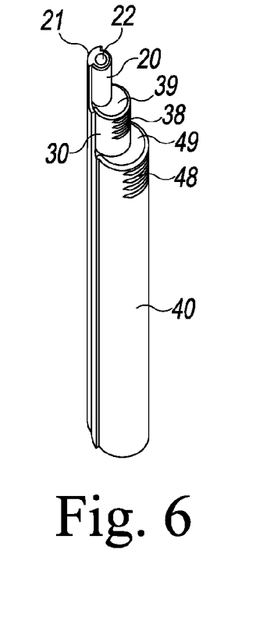
FIG. 6 is an isometric view of the initial dilation tube, the secondary dilation tube and a tertiary dilation tube assembled thereon of the exemplary dilation tube system of FIG. 1.
Figure 7:
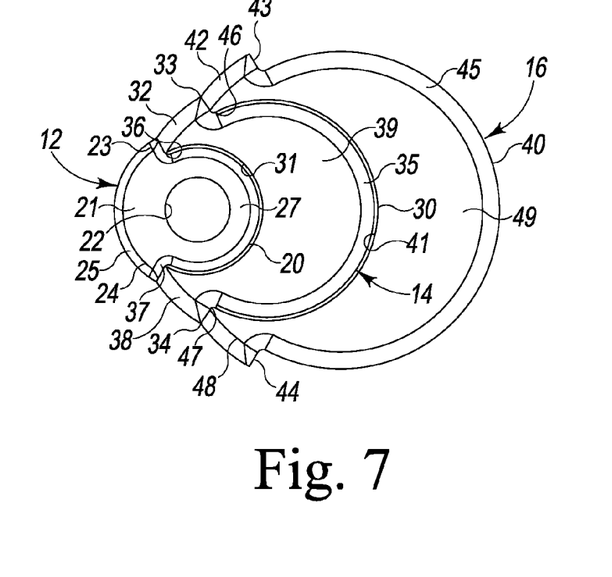
FIG. 7 is an enlarged top view of the assembled initial, secondary and tertiary dilation tubes of FIG. 6.

Referring to FIGS. 6 and 7 there is depicted a third stage in assembly of the dilation tube structure 10 wherein the second subsequent directional dilation tube 16 is situated onto the first subsequent directional dilation tube 14. The outer shape and configuration of the first subsequent directional dilation tube 14 allows nested reception of the second subsequent directional dilation tube 16. The second subsequent directional dilation tube 16 is defined by a generally elliptic cylinder body 40 having a rounded outer surface and a rounded longitudinal notch, cutout, channel or the like 41. An upper end 49 of the body 40 is generally planar. The longitudinal channel 41 extends the length of the elliptic cylinder body 40 and provides a reception site for the first subsequent directional dilation tube 14 as the second subsequent directional dilation tube 16 is received onto the first subsequent directional dilation tube 14 during the third stage of incision dilation per the present method. The outer surface of the body 40 is preferably smooth, including the inner surface of the longitudinal channel 41. An upper portion of the outer surface of the body 30 may include arced notches 48.

Referring to FIG. 7, an enlarged view of a top of the second subsequent directional dilation tube 16 is shown to particularly envision its longitudinal and cross-sectional shape and/or configuration. As discerned, the longitudinal channel 41 has a rounded inner surface, shape and size complementary to the outer surface of the body 30 of the first subsequent directional dilation tube 14 in order to be received on the first subsequent directional dilation tube 14. Nesting structures include a first longitudinal flange 42 provided at a first edge or end 46 of the channel 41 and a second longitudinal flange 48 provided at a second edge or end 47 of the channel 41. Others are provided, including the shape of the first end 46 being complementary to the shape of the first transition 33 such that the first end 46 of the second subsequent directional dilation tube 16 seats or nests against the first transition 33 of the first subsequent dilation tube 14. The shape of the second end 47 is complementary to the shape of the second transition 34 such that the second end 47 of the second subsequent directional dilation tube 16 seats or nests against the second transition 34 of the first subsequent directional dilation tube 14. A beveled or angled edge 45 provides a transition between the upper ends of the body 40 and first and second flanges 42, 48.

The first flange 42 extends from the body 40 at a first longitudinal transition 43 and is generally arc-shaped and preferably, but not necessarily, concentric with the outer surface of the body 40. The second flange 48 extends from the body 40 at a second longitudinal transition 44 and is generally arc-shaped and preferably, but not necessarily, concentric with the outer surface of the body 40. The first longitudinal transition 43 creates or defines a first shelf or ledge providing a first seat for a third subsequent dilation tube 18. The second longitudinal transition 44 creates or defines a second shelf or ledge providing a second seat for the third subsequent directional dilation tube 18. As seen in FIG. 11, the second subsequent directional dilation tube 16 has a beveled lower end 70.

The second subsequent directional dilation tube 16 is configured as an elliptical cylinder with the channel 41 disposed in a side thereof. As such the tube 16 has an elliptic portion 49 that projects outwardly from the channel 41. Direction of the elliptic portion 49 provides the direction of incision dilation which coincides with the direction of the elliptic portion 39 of the first subsequent directional dilation tube 14.

The second subsequent directional dilation tube 16 is the third dilation tube to be inserted into the incision. The bore 22 of the initial dilation tube 12 still permits monitoring position of the nerve or nerves (neuro-monitoring) while the incision is further dilated away from the nerve (e.g. anteriorly) in the desired angle as determined by the rotational orientation of the initial dilation tube 12. In this third stage of incision dilation, the second subsequent directional dilation tube 16 inserted over the first subsequent directional dilation tube 14 and into the incision. The elliptical configuration of the body 40 further migrates the incision dilation towards the direction of the ellipse. The nesting structures provide a stable construct. Moreover, the nesting structures allow one dilation tube to be precisely assembled onto the previous dilation tube from the vertical position, essentially vertically sliding one dilation tube onto the other dilation tube.

Figures 8, 9, 10:
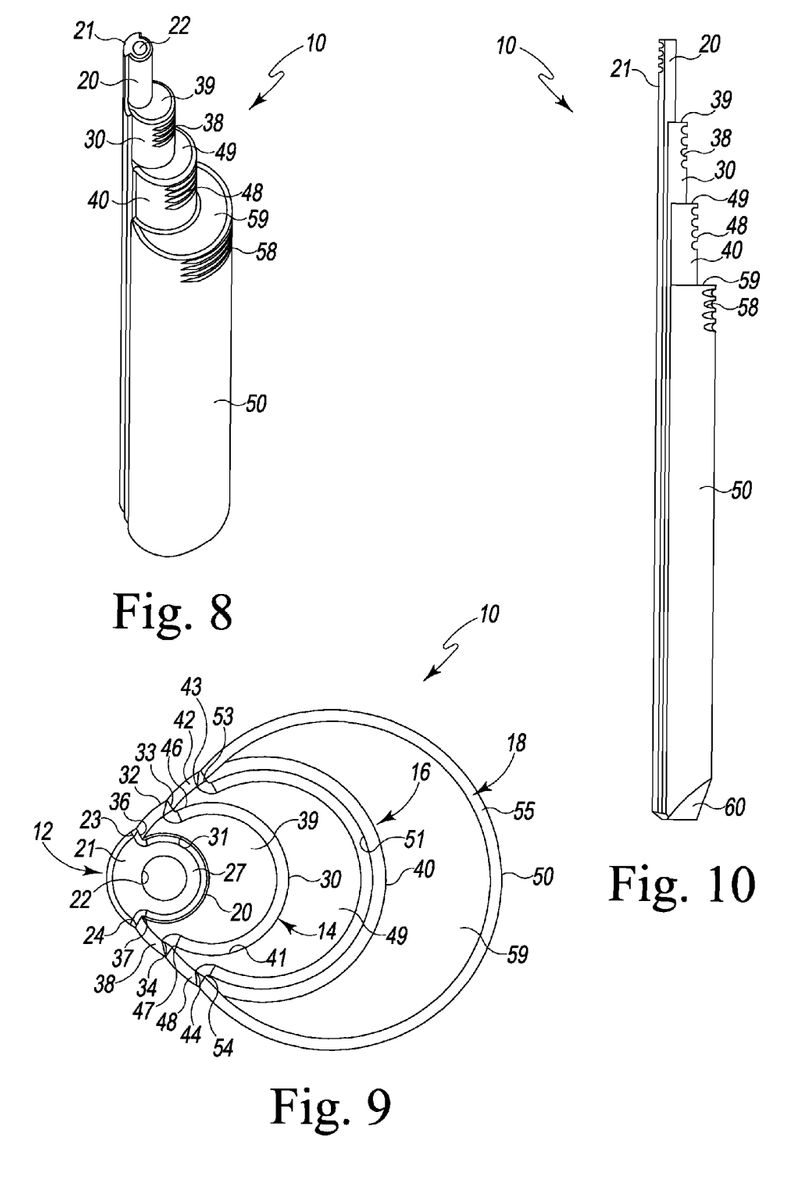
FIG. 8 is an isometric view of the initial dilation tube, the secondary dilation tube, the tertiary dilation tube and a quaternary dilation tube assembled thereon of the exemplary dilation tube system of FIG. 1.
FIG. 9 is an enlarged top view of the initial, secondary, tertiary and quaternary dilations tubes of FIG. 8.
FIG. 10 is a side view of the assembled initial, secondary, tertiary and quaternary dilations tubes of the present invention.

Referring to FIGS. 8 and 9 there is depicted a fourth, and with this embodiment of dilation tube assembly, a final stage in assembly of the dilation tube structure 10 wherein the third subsequent directional dilation tube 18 is situated onto the second subsequent directional dilation tube 16. The outer shape and configuration of the second subsequent directional dilation tube 16 allows nested reception of the third subsequent directional dilation tube 18 in like manner to the previous dilation tubes. The third subsequent directional dilation tube 18 is defined by a generally elliptic cylinder body 50 having a rounded outer surface and a rounded longitudinal notch, cutout, channel or the like 51. An upper end 59 of the body 50 is generally planar. The longitudinal channel 51 extends the length of the elliptic cylinder body 50 and provides a reception site for the second subsequent directional dilation tube 16 as the third subsequent directional dilation tube 18 is received onto the second subsequent directional dilation tube 16 during the fourth stage of incision dilation per the present method. The outer surface of the body 50 is preferably smooth, including the inner surface of the longitudinal channel 51. An upper portion of the outer surface of the body 50 may include arced notches 58.

Referring to FIG. 9, an enlarged view of a top of the third subsequent dilation tube 18 is shown to particularly envision its longitudinal and cross-sectional shape and/or configuration. As discerned, the longitudinal channel 51 has a rounded inner surface, shape and size complementary to the outer surface of the body 40 of the second subsequent dilation tube 16 in order to be received on the second subsequent dilation tube 16. A first edge 53 is provided at a first end of the channel 51, while a second edge 54 is provided at a second end of the channel 51. Again, the tube has nesting structures. The shape of the first end 53 is complementary to the shape of the first transition 43 such that the first end 53 of the third subsequent directional dilation tube 18 seats or nests against the first transition 43 of the second subsequent directional dilation tube 16. The shape of the second end 54 is complementary to the shape of the second transition 44 such that the second end 54 of the third subsequent directional dilation tube 18 seats or nests against the second transition 4 of the second subsequent directional dilation tube 16. A beveled or angled edge 55 provides a transition between the upper ends of the body 50 and first and second ends 53, 54. As seen in FIG. 11, the third subsequent directional dilation tube 18 has a beveled lower end 60.

The third subsequent directional dilation tube 18 is configured as an elliptical cylinder with the channel 51 disposed in a side thereof. As such the tube 18 has an elliptic portion 59 that projects outwardly from the channel 51. Direction of the elliptic portion 59 provides the direction of incision dilation which coincides with the direction of the elliptic portion 49 of the second subsequent directional dilation tube 16.

The third subsequent directional dilation tube 18 is the fourth (and here, final) dilation tube to be inserted into the incision. The bore 22 of the initial dilation tube 12 still permits monitoring position of the nerve or nerves (neuro-monitoring) while the incision is further dilated away from the nerve (e.g. anteriorly) in the desired angle as determined by the rotational orientation of the initial dilation tube 12. In this fourth stage of incision dilation, the third subsequent directional dilation tube 18 inserted over the second subsequent directional dilation tube 16 and into the incision. The elliptical configuration of the body 50 further migrates the incision dilation towards the direction of the ellipse. FIG. 10 depicts a side view of all of the dilation tubes assembled (i.e. the present dilation tube assembly 10).

It should be appreciated that more subsequent dilation tubes having like configurations may be position between the initial dilation tube and the final dilation tube.

Figure 12:
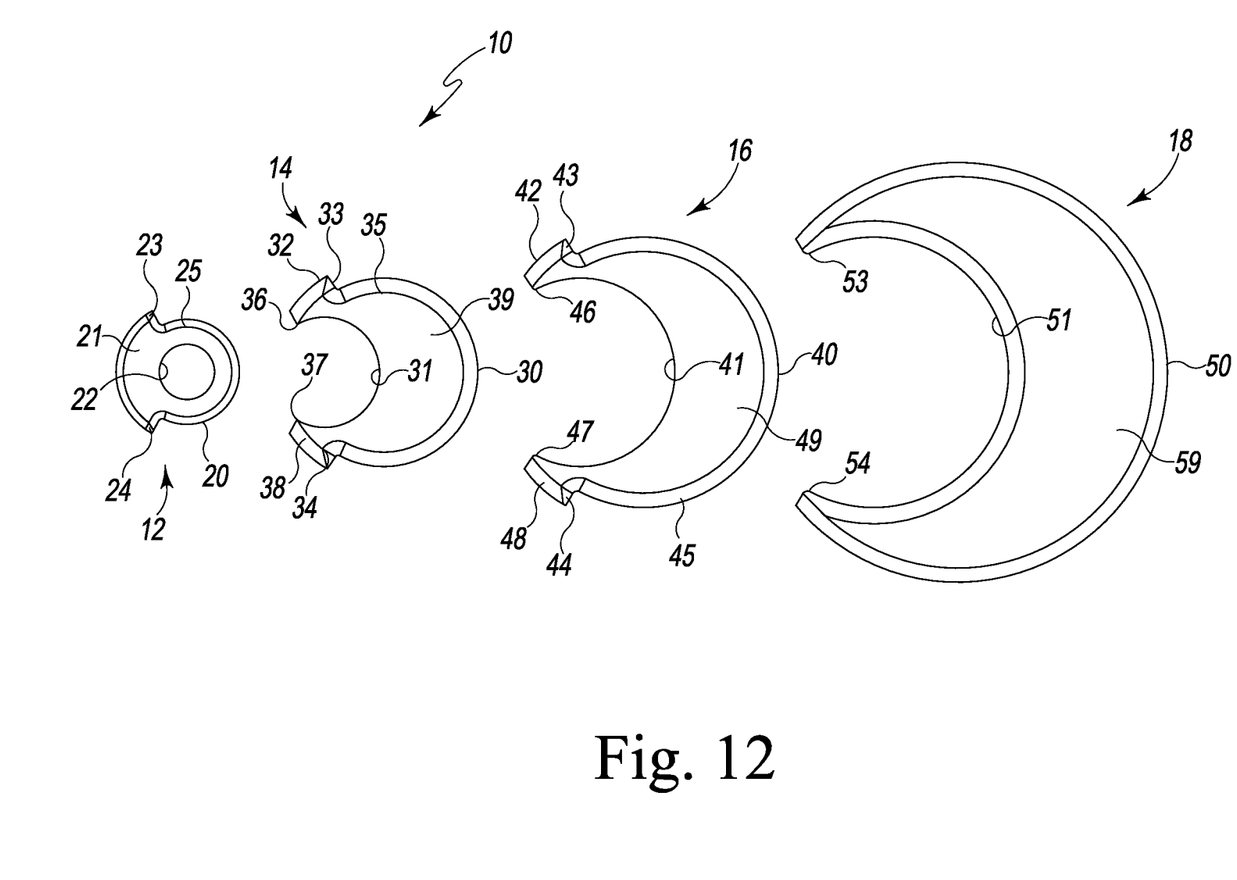
FIG. 12 is a top exploded view of the initial, secondary, tertiary and quaternary dilations tubes.

FIG. 12 shows the four directional dilation tubes in an exploded view to illustrate how the various dilation tubes are received on one another and nest together.

Figure 13:
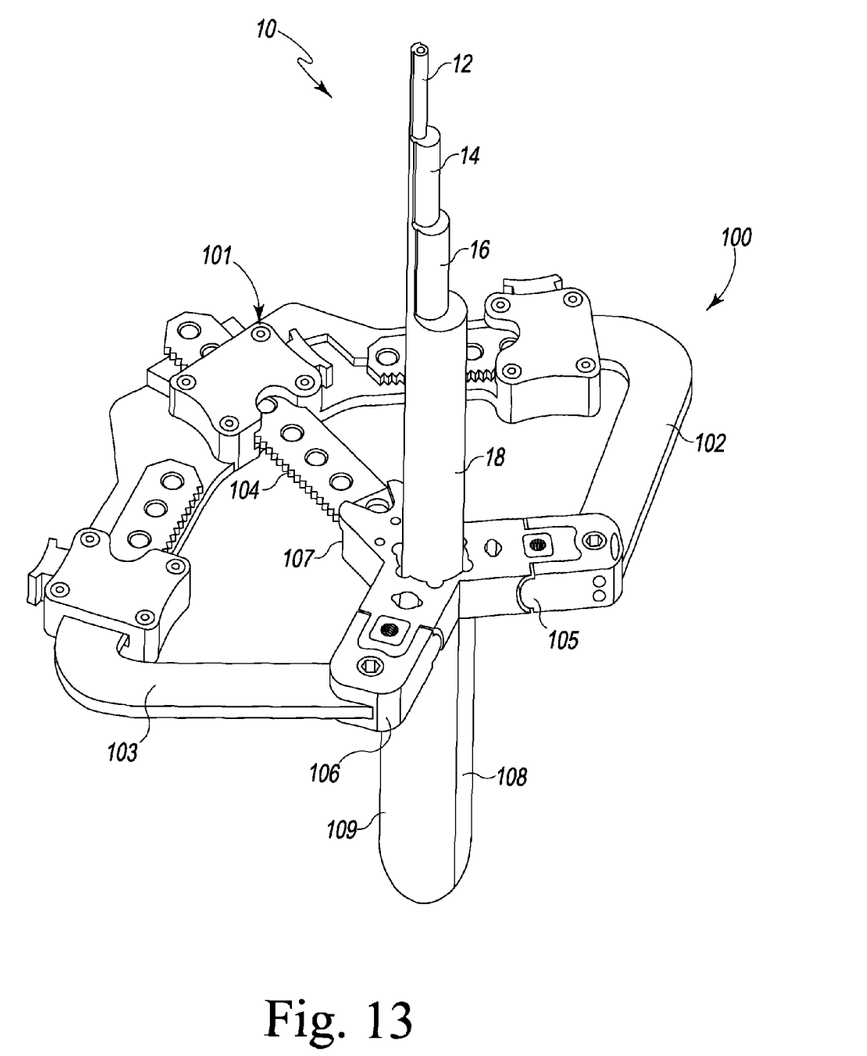
FIG. 13 is an isometric view of a spinal retractor holding the dilation tube system of FIG. 1.
Figure 14:
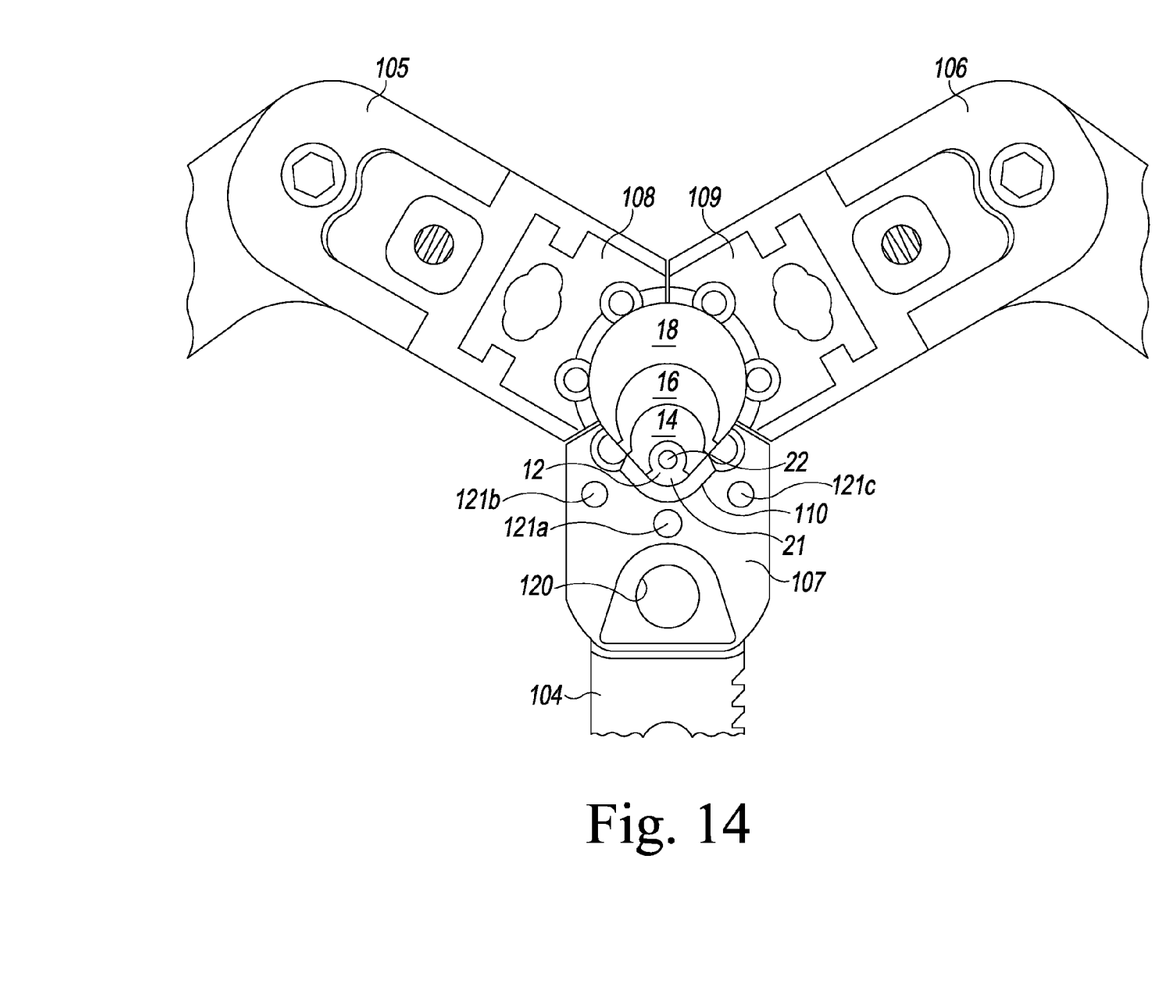
FIG. 14 is an enlarged top view of a portion of the spinal retractor holding the dilation tube system of FIG. 13.

FIGS. 13 and 14 show the spinal retractor 100 holding the present directional dilation tube assembly 10. The retractor 100 has a body 101 that is configured to be mounted relative to a spine patient via a threaded bore (or attachment location) 120 of the static arm 107 of the body 101. The body 101 has a first adjustable arm 102 that holds an articulating portion 105, and a second adjustable arm 103 that holds an articulating portion 106. The articulating portion 105 is configured to receive a blade 108, while the articulating portion 107 is configured to receive a blade 109. The arm 104 may or may not be static regarding articulation and holds the configured blade 110. The arm 104 may also have guide holes 121a, 121b, and 121c posterior of the wall of the static blade 110 for insertion of a neuro-monitoring sounding probe following insertion of the retractor blades if double checking of nerve position is desired. The arm 104 may hold the blade 110 static such that the blade 110 has no angulation capabilities for additional rigidity of the construct.

A more complete description of a spinal retractor such as can be used in place of retractor 100, with the exception of a static posterior blade 110, is found in U.S. patent application Ser. No. 13/720,800 filed Dec. 19, 2012, the specification of which is specifically incorporated herein by reference.

Figure 15:
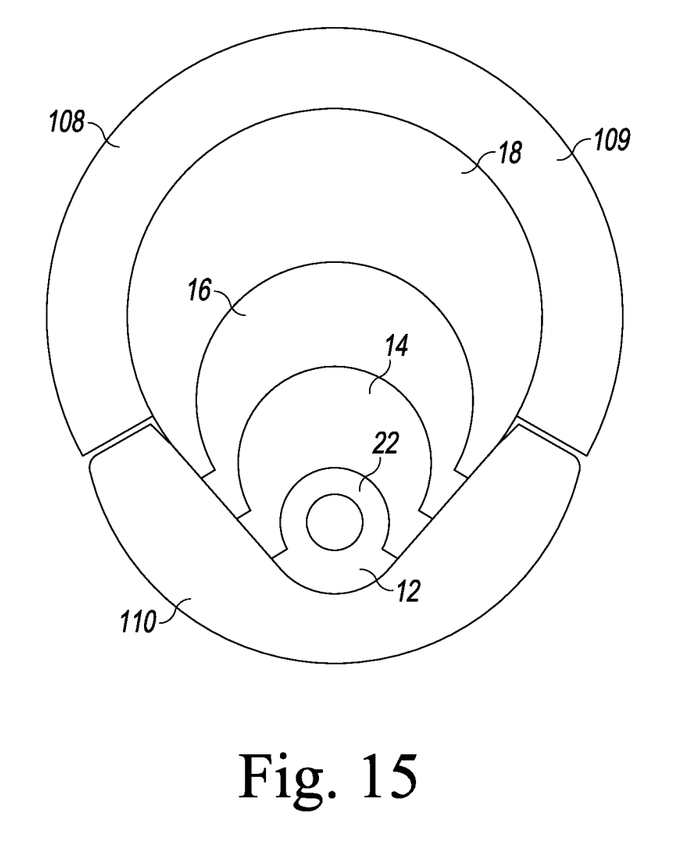
FIG. 15 is an enlarged cross sectioned top view of the present assembled dilation tube system surrounded by blades of the spinal retractor particularly illustrating the directional dilation migration at a given distance or angle from an initial insertion point achieved by the present dilation tube system.

FIG. 15 is an illustration depicting the directional dilation tube assembly 10 surrounded by the blades 108, 109 and 110 of the retractor 100 particularly showing the configuration of the static blade 110 for receiving the stacked configuration of dilation tubes 12, 14, 16, 18. As easily discerned, the bore 22 of the initial dilation tube 12 permits monitoring position of a nerve or nerves while migrating the incision dilation towards the elliptic portions of the tubes.

Figure 16:
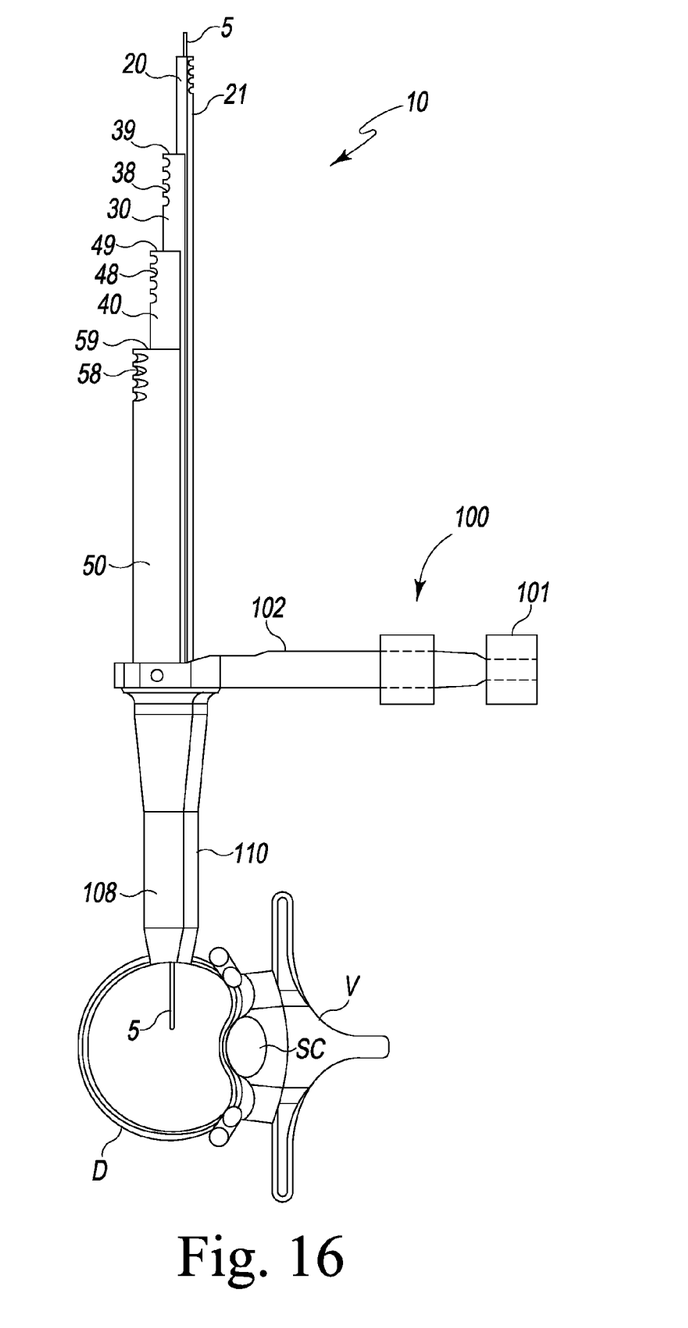
FIG. 16 is a side view of the present assembled dilation tube system with an inserted neuro probe held by the spinal retractor of FIG. 15 relative to a vertebral section of a patient.

FIG. 16 shows the directional dilation tube assembly 10 held by the retractor 100 relative to a human vertebral section, particularly a vertebra V, spinal column SC, and vertebral disc D. The directional dilation tube assembly 10 has been fully assembled and a neuro monitoring probe, device or the like 5 extends through the bore 22 of the initial dilation tube 12 from an upper end of the body 20 to a lower end of the body 20. FIG. 16 provides an exemplary manner of using the present directional dilation tube assembly 10.

While the invention has been illustrated and described in detail in the drawings and foregoing description, the same is to be considered as illustrative and not restrictive in character, it being understood that preferred embodiments have been shown and described and that all changes and modifications that come within the spirit of the invention are desired to be protected.

What is claimed is:

1. A directional incision dilation tube assembly comprising:
  a non-directional first dilation tube comprising a first body having a first size, a longitudinal projection extending from the first body, a first longitudinal recess located between the longitudinal projection and the first body and a second longitudinal recess located between the projection and the first body;
  a directional second dilation tube comprising:
    a second body having a generally elliptical cross section of a second size which is greater than the first size,
    first and second spaced apart flanges extending from the second body, wherein the first flange engages the first longitudinal recess of the first dilation tube, and wherein the second flange engages the second longitudinal recess of the first dilation tube,
    a first longitudinal recess located between the first flange and the second body,
    a second longitudinal recess located between the second flange and the second body, and
    a first longitudinal channel defined by the first flange, the second flange, and the second body, wherein the longitudinal channel is configured to receive the first body of the first dilation tube;
  a directional third dilation tube comprising:
    a third body having a generally elliptical cross section of a third size which is greater than the second size,
    first and second spaced apart flanges extending from the third body, wherein the first flange engages the first longitudinal recess of the second dilation tube, and the second flange engages the second longitudinal recess of the second dilation tube,
    a first longitudinal recess located between the first flange and the third body and
    a second longitudinal recess located between the second flange and the third body,
    a second longitudinal channel defined by the first flange, the second flange, and the third body, wherein the second longitudinal channel is configured to receive the second body of the second dilation tube; and
  a directional fourth dilation tube comprising:
    a fourth body having a generally elliptical cross section of a fourth size which is greater than the third size,
    first and second spaced apart flanges extending from the fourth body, wherein the first flange engages the first longitudinal recess of the third dilation tube, and the second flange engages the second longitudinal recess of the third dilation tube,
    a first longitudinal recess located between the first flange and the fourth body and
    a second longitudinal recess located between the second flange and the fourth body,
    a third longitudinal channel defined by the first flange, the second flange, and the fourth body, wherein the third longitudinal channel is configured to receive the third body of the third dilation tube.

2. The directional incision dilation tube assembly of claim 1, wherein the longitudinal projection is formed on and extends from an outer, generally round surface of the non-directional first dilation tube.

3. The directional incision dilation tube assembly of claim 1, wherein:
  the first flange of the second dilation tube comprises a first end to seat within the first longitudinal recess of the first dilation tube;
  the second flange of the second dilation tube comprises a second end to seat within the second longitudinal recess of the first dilation tube.

4. The directional incision dilation tube assembly of claim 3, wherein:
  the first flange of the third dilation tube comprises a first end to seat within the first longitudinal recess of the second dilation tube;
  the second flange of the third dilation tube comprises a second end to seat within the second longitudinal recess of the second dilation tube.

5. The directional incision dilation tube assembly of claim 4, wherein the projection and the first and second flanges of the second, third, and fourth dilation tubes are configured to be adjacent one another when the second, third, and fourth directional dilation tubes are sequentially assembled onto the first dilation tube so that the outer surface of the fourth dilation tube, first and second flanges of the second directional dilation tube, first and second flanges of the third directional dilation tube, and the projection of the first dilation tube substantially form an outer surface of the directional incision dilation tube assembly.

6. A sequential directional incision dilation tube assembly comprising:
  a non-directional dilation tube comprising a body, a longitudinal projection, and a first longitudinal recess located between the longitudinal projection and the body, and second longitudinal recess located between the longitudinal projection and the body;
  one or more inner directional dilation tubes, each comprising:
    a body,
    first and second spaced apart flanges extending from the body,
    a first longitudinal recess located between the first flange and the body,
    a second longitudinal recess located between the second flange and the body,
    a longitudinal channel defined by the first flange, the second flange, and the body,
    wherein the longitudinal channel is configured to receive the body of an adjacent directional dilation tube or the non-directional dilation tube,
    wherein the first flange engages the first longitudinal recess of the adjacent dilation tube or the non-directional dilation tube, and the second flange engages the second longitudinal recess of the adjacent directional dilation tube or the non-directional dilation tube;
  an outer directional dilation tube comprising:
    a body,
    first and second spaced apart flanges extending from the body,
    a first longitudinal recess located between the first flange and the body,
    a second longitudinal recess located between the second flange and the body,
    a longitudinal channel defined by the first flange, the second flange, and the body, the channel sized to be received on and immediately over an adjacent one of the one or more inner directional dilation tubes;
    wherein the first flange engages the first longitudinal recess of the adjacent inner directional dilation tube, and the second flange engages the second longitudinal recess of the adjacent inner directional dilation tube;

wherein the outer surface of the outer directional dilation tube, first and second flanges of the one or more inner directional dilation tubes, and the projection of the non-directional dilation tube substantially form an overall outer surface of the directional incision dilation tube assembly.

7. The sequential directional incision dilation tube assembly of claim 6, wherein the longitudinal projection is formed on an outer, generally round surface of the non-directional dilation tube and defining a first longitudinal side surface and a second longitudinal side surface.

8. The sequential directional incision dilation tube assembly of claim 6, wherein:
   each of the first flanges comprises a first end to seat within the adjacent longitudinal recess;
   each of the second flanges comprises a second end to seat within the adjacent longitudinal recess.

9. The directional incision dilation tube assembly of claim 8, wherein the channel on the outer directional dilation tube is defined by a first longitudinal edge and a second longitudinal edge, the first longitudinal edge seats within the first longitudinal recess of the adjacent one of the dilation tubes, and the second longitudinal edge seats within the second longitudinal recess of the adjacent one of the dilation tubes.

10. The directional incision dilation tube assembly of claim 9, wherein each of the first and second flanges are configured to be adjacent one another when the directional dilation tubes are sequentially assembled onto the non-directional dilation tube.

11. A method of neuro monitoring and sequential directional incision dilation for spinal surgery, the method comprising:
   providing a dilation tube assembly comprising:
      a non-directional dilation tube comprising a body, a longitudinal projection, and a first longitudinal recess located between the longitudinal projection and the body, and a second longitudinal recess located between the longitudinal projection and the body;
   one or more directional dilation tubes, each directional dilation tube comprising:
      a body,
      first and second spaced apart flanges extending from the body,
      a first longitudinal recess located between the first flange and the body,
      a second longitudinal recess located between the second flange and the body,
      a longitudinal channel defined by the first flange, the second flange, and the body,
      wherein the longitudinal channel is configured to receive the body of an adjacent directional dilation tube or the non-directional dilation tube,
      wherein the first flange engages the first longitudinal recess of either an adjacent dilation tube or the non-directional dilation tube, and the second flange engages the second longitudinal recess of either the adjacent directional dilation tube or the non-directional dilation tube;
   wherein an outer surface of an outer directional dilation tube, first and second flanges of any additional directional dilation tubes, and the projection of the non-directional dilation tube substantially form an overall outer surface of the directional incision dilation tube assembly;
   inserting the non-directional dilation tube into an incision; and
   sequentially connecting the one or more directional dilation tubes onto the non-directional dilation tube and over any previously connected directional dilations tubes.

* * * * *